United States Patent
Yan et al.

(10) Patent No.: US 9,161,985 B2
(45) Date of Patent: Oct. 20, 2015

(54) 5α-ANDROSTANE (ALKYL)-3β, 5, 6β-TRIOL INJECTION AND PREPARATION METHOD THEREFOR

(75) Inventors: Guangmei Yan, Guangzhou (CN); Haiyan Hu, Guangzhou (CN); Jingxia Zhang, Guangzhou (CN); Pengxin Qiu, Guangzhou (CN); Ling Li, Guangzhou (CN); Ning Tian, Guangzhou (CN)

(73) Assignee: Guangzhou Cellprotek Pharmaceutical Ltd., Guangzhou (CN)

( * ) Notice: Subject to any disclaimer, the term of this patent is extended or adjusted under 35 U.S.C. 154(b) by 31 days.

(21) Appl. No.: 13/821,849

(22) PCT Filed: Jul. 8, 2011

(86) PCT No.: PCT/CN2011/076968
§ 371 (c)(1),
(2), (4) Date: Mar. 8, 2013

(87) PCT Pub. No.: WO2012/037834
PCT Pub. Date: Mar. 29, 2012

(65) Prior Publication Data
US 2013/0172307 A1    Jul. 4, 2013

(30) Foreign Application Priority Data
Sep. 21, 2010 (CN) .............. 20100292234

(51) Int. Cl.
| A61K 31/56 | (2006.01) |
| A61K 47/40 | (2006.01) |
| A61K 9/00 | (2006.01) |
| A61K 31/565 | (2006.01) |
| A61K 47/48 | (2006.01) |
| B82Y 5/00 | (2011.01) |
| A61K 31/568 | (2006.01) |

(52) U.S. Cl.
CPC .............. *A61K 47/40* (2013.01); *A61K 9/0019* (2013.01); *A61K 31/565* (2013.01); *A61K 31/568* (2013.01); *A61K 47/48969* (2013.01); *B82Y 5/00* (2013.01)

(58) Field of Classification Search
None
See application file for complete search history.

(56) References Cited

U.S. PATENT DOCUMENTS

2003/0060425 A1* 3/2003 Ahlem et al. ............... 514/26

FOREIGN PATENT DOCUMENTS

| CN | 1201397 A | 12/1998 |
| CN | 1706501 A | 12/2005 |
| WO | WO 97/17992 A1 | 5/1997 |

OTHER PUBLICATIONS

Ohuchi et al.( Chem. Pharm. Bull. (1981) vol. 29, pp. 45-50).*
Jingbo Chen et al.; "Hemisuccination of Hydroxysterols" Hecheng Huzxue, 2000, vol. 8, No. 5, pp. 466-468, (2000).
International Search Report from the Chinese Patent Office for International Application No. PCT/CN2011/076968, mailing date Oct. 13, 2011.

* cited by examiner

Primary Examiner — Anna Pagonakis
Assistant Examiner — Jared D Barsky
(74) Attorney, Agent, or Firm — Finnegan, Henderson, Farabow, Garrett & Dunner LLP

(57) ABSTRACT

A 5α-androstane-3β,5,6β-triol injection and its preparation are disclosed. The injection uses hydroxypropyl-β-cyclodextrin as a solubilizing agent and the active ingredient is present at a weight ratio of 1-20:40-500 to the hydroxypropyl-β-cyclodextrin. The injection may also comprise, by weight, 1-100 parts of at least one isotonic adjusting agent, 0-200 parts of at least one freeze drying filler, and 0-2000 parts of at least one solvent. The preparation method comprises dissolving hydroxypropyl-β-cyclodextrin solution, 5α-androstane-3β,5,6β-triol and at least one additional soluble excipient in water for injection in sequence to obtain a raw injection solution, and subjecting the raw injection solution to decolorization, depyrogenation, filtration and sterilization to obtain the injection, Drying the filtrate yields a solid for injection.

7 Claims, No Drawings

5α-ANDROSTANE (ALKYL)-3β, 5, 6β-TRIOL INJECTION AND PREPARATION METHOD THEREFOR

This application is the U.S. National Stage Application of PCT/CN2011/076968, filed Jul. 8, 2011, which claims priority to Chinese Patent Application No. 201010292234.X, filed Sep. 21, 2010, all of which are incorporated herein by reference.

FIELD OF THE TECHNOLOGY

The present invention is in the field of pharmaceutics and relates to 5α-androstane-3β,5,6β-triol injection and its preparation method.

BACKGROUND

5α-androstane-3β,5,6β-triol (hereinafter YC-6) is a newly-found neuron protective compound. Currently, Acute Ischemic Stroke (AIS) is treated mainly by thrombolytic or neuron protective therapy. Neuron protective agents can reduce cerebral infarction area, avoid hemorrhage, and prevent complications that may occur during thrombolytic or anticoagulant therapy. Moreover, it can be used even without any detailed aetiological diagnosis and make early treatment possible. Neuron protective agents have therefore attracted increasing attention in AIS research.

However, no neuron protective agent has been proven to be safe and effective so far. A lot of compounds with potential value for clinical application are under clinical trials, including calcium channel blockers (CCB), calcium channel modulators, glutamate release inhibitors, γ-aminobutyric acid (GABA) receptor agonists, free radical scavengers, anti-intercellular adhesion molecule antibodies, and so on. Among a large number of compounds, neuro-active steroids are increasingly attractive due to their extensive effect of neuron protection. In particular, the effect of compound YC-6, as a newly-found neuron protective chemical entity, is not limited to neuron protection. It is effective against not only cerebral ischemia but also spinal cord ischemia at a daily dose of 50-100 mg.

YC-6 has low solubility in water. Although its solubility can be increased in conventional non-aqueous solvents or mixtures thereof, these solvents cause irritation, and the precipitation of YC-6 might occur when diluted with water. The efficacy and safety of YC-6 injection are therefore adversely affected and the use thereof is limited.

SUMMARY OF THE INVENTION

To overcome the deficiencies set forth above, YC-6 injections and their preparation methods are provided by the present invention. The present invention uses hydroxypropyl-β-cyclodextrin as a solubilizing agent to prepare YC-6 injections. The irritation caused by non-aqueous solvents is successfully cut down while the solubility of YC-6 is increased.

To achieve this, YC-6 injections are provided in liquid or solid form. The injections have at least one soluble excipient comprising hydroxypropyl-β-cyclodextrin. The at least one soluble excipient can also comprise at least one isotonic adjusting agent and/or at least one freeze drying filler.

Preferably, the weight ratio of YC-6 versus hydroxypropyl-β-cyclodextrin is 1-20:40-500.

The injections can also comprise the following components (by weight): 1-20 parts of YC-6, 40-500 parts of hydroxypropyl-β-cyclodextrin, 1-100 parts of at least one isotonic adjusting agent, 0-200 parts of at least one freeze drying filler, and 0-2000 parts of at least one solvent.

The at least one isotonic adjusting agent is selected from sodium chloride, glucose, mannitol, lactose, xylitol, sorbitol, maltitol, and combinations thereof.

The at least one freeze-drying filler is selected from sodium chloride, glucose, mannitol, lactose, xylitol, sorbitol, maltitol, and combinations thereof.

If a liquid injection is to be prepared, the at least one solvent is selected from propanediol, ethanol, polyethylene glycol 400, polyethylene glycol 200, glycerol, and water.

The liquid injection of the present invention can be prepared by a method comprising:
dissolving hydroxypropyl-β-cyclodextrin, YC-6 and at least one additional soluble excipient in water for injection in sequence to obtain a raw solution; and
subjecting the raw solution to decolorization, filtration, and sterilization to obtain the injection of the present invention.

Freeze-drying powder is prepared by a method comprising:
filling a filtrate produced by the filtration step in the above liquid injection preparation method into an ampoule and freeze-drying the filtrate in the ampoule.

Sterile powder is prepared by a method comprising:
spray drying a filtrate produced by the filtration step in the above liquid injection preparation method, and
packaging the resulting sterilized powder.

The decolorization can be performed by using activated carbon at an amount ranging from 0.1-0.3% by weight of the injection and the sterilization can be performed at 115° C. for 30 min or at 121° C. for 15 min.

It will be appreciated that the YC-6 can also be formulated into YC-6-loaded infusions, through mixing YC-6 injection with conventional drug-free infusions such as glucose infusion, sodium chloride infusion or glucose and sodium chloride infusion.

The present invention is advantageous over conventional techniques. Uses of hydroxypropyl-β-cyclodextrin or non-aqueous solvents/mixed solvents increase the solubility of YC-6, so that YC-6 can be prepared into liquid injection comprising water, non-aqueous solvent, or mixture of solvents, sterile powder, freeze drying powder, YC-6-loaded glucose infusion, sodium chloride infusion, or glucose and sodium chloride infusion, which makes possible for YC-6 to be administrated by intravenous injection in case of emergency. In addition, YC-6 injection of the present invention has sufficient solubility and efficacy without any irritation. The preparation process is also simple and widely available.

DETAILED DESCRIPTION OF THE INVENTION

Example 1

Preparation of 200 Ampoules of YC-6 Liquid Injection (Specification 5 ml:50 mg)

Formula:

| | |
|---|---|
| YC-6 | 10 g |
| 2-hydroxypropyl-β-cyclodextrin | 200 g |
| Sodium chloride | 1.25 g |
| Water for injection | qs 1000 ml |

Preparation: 2-hydroxypropyl-β-cyclodextrin was dissolved in 80% of the fresh water for injection and YC-6 was added. The resulting mixture was stirred at room temperature for 10-20 min to make YC-6 completely dissolved. Sodium chloride was added and dissolved by stirring. Water was added to make the volume to 1000 ml. Activated charcoal (0.1%) was added into the above solution, which was stirred for 15 min at 60° C. and then was allowed to cool down to room temperature. A 0.22 μm microporous membrane filter was used to filter the solution. The filtrate was collected and filled to prepare 5 ml injection, which was then subjected to sterilization at 121° C. for 15 min.

Example 2

Preparation of 200 Ampoules of YC-6 Liquid Injection (Specification 10 ml:80 mg)

Formula:

| | |
|---|---|
| YC-6 | 16 g |
| 3-hydroxypropyl-β-cyclodextrin | 400 g |
| Glucose | 13.9 g |
| Water for injection | qs 2000 ml |

Preparation: 3-Hydroxypropyl-β-cyclodextrin was dissolved in 80% of the fresh water for injection and YC-6 was added. The resulting mixture was stirred at room temperature for 10-20 min to make YC-6 completely dissolved. Glucose was added and dissolved by stirring. Water was added to make the volume to 2000 ml. Activated charcoal (0.1%) was added into the above solution, which was stirred for 15 min at 60° C. and then allowed to cool naturally to room temperature. A 0.22 μm microporous membrane filter was used to filter the solution. The filtrate was collected and filled to prepare 10 ml injection, which was then subjected to sterilization at 121° C. for 15 min.

Example 3

Preparation of 200 Ampoules of YC-6 Liquid Injection (Specification 5 ml: 100 mg)

Formula:

| | |
|---|---|
| YC-6 | 20 g |
| 2-hydroxypropyl-β-cyclodextrin | 400 g |
| Water for injection | qs 1000 ml |

Preparation: 2-Hydroxypropyl-β-cyclodextrin was dissolved in 80% of the fresh water for injection and YC-6 was added. The resulting mixture was stirred at room temperature for 10-20 min to make YC-6 completely dissolved. Water was added to make the volume to 1000 ml. Activated charcoal (0.1%) was added into the above solution, which was stirred for 15 min at 60° C. and allowed to cool naturally to room temperature. A 0.22 μm microporous membrane filter was used to filter the solution. The filtrate was collected and filled to prepare 5 ml injection, which was then subjected to sterilization at 115° C. for 30 min.

Example 4

Preparation of 200 Ampoules of YC-6 Sterile Powder (Specification 80 mg/Bottle)

Formula:

| | |
|---|---|
| YC-6 | 16 g |
| 2-hydroxypropyl-β-cyclodextrin | 400 g |
| Sodium chloride | 2.5 g |
| Packaged into | 200 ampoules |

Preparation: 2-Hydroxypropyl-β-cyclodextrin was dissolved in 80% of the fresh water for injection and YC-6 was added. The resulting mixture was stirred at room temperature for 10-20 min to make YC-6 completely dissolved. Sodium chloride was added and dissolved by stirring. Water was added to make the volume to 2000 ml. Activated charcoal (0.1%) was added into the above solution, which was stirred for 15 min at 60° C. and then allowed to cool naturally to room temperature. A 0.22 μm microporous membrane filter was used to filter. The filtrate was subjected to spray drying and then packaged into 200 ampoules.

Example 5

Preparation of 200 Ampoules of YC-6 Freeze Drying Powder (Specification 5 ml:60 mg)

Formula:

| | |
|---|---|
| YC-6 | 12 g |
| 3-hydroxypropyl-β-cyclodextrin | 200 g |
| Glucose | 7 g |
| Water for injection | qs1000 ml |

Preparation: 3-Hydroxypropyl-β-cyclodextrin was dissolved in 80% of the fresh water for injection and YC-6 was added. The resulting mixture was stirred at room temperature for 10-20 min to make YC-6 completely dissolved. Glucose was added and dissolved by stirring. Water was added to make the volume to 1000 ml. Activated charcoal (0.1%) was added into the above solution, which was stirred for 15 min at 60° C. and allowed to cool naturally to room temperature. A 0.22 μm microporous membrane filter was used to filter the solution. The filtrate was packaged into 5 ml ampoules and then was subjected to freeze drying.

Example 6

Compatible Stability of YC-6 Injection and Conventional Infusions

Two ampoules of YC-6 injection (5 ml×2) of Example 1 were added to conventional infusions to evaluate the compatible stability of YC-6 therein in 8 h. Compatible stability was evaluated in terms of color, clarity, pH and YC-6 content. Results are shown in the following tables.

TABLE 1

Compatibility tests of YC-6 injection and conventional infusions

| ID | Compatibility tests (25-30° C.) |
|---|---|
| A | YC-6 injection 5 ml × 2 + 5% glucose injection 250 ml |
| B | YC-6 injection 5 ml × 2 + 0.9% sodium chloride injection 250 ml |
| C | YC-6 injection 5 ml × 2 + glucose and NaCl injection 250 ml |
| D | YC-6 injection 5 ml × 2 + compound NaCl injection 500 ml |
| E | YC-6 injection 5 ml × 2 + 5% sodium bicarbonate injection 250 ml |

TABLE 2

Changes in color and clarity of conventional infusions

| ID | Prior to adding | After adding (h) | | | |
|---|---|---|---|---|---|
| | | 0 | 2 | 4 | 8 |
| A | Colorless, clear | Colorless, clear | Colorless, clear | Colorless, clear | Colorless, clear |
| B | Colorless, clear | Colorless, clear | Colorless, clear | Colorless, clear | Colorless, clear |
| C | Colorless, clear | Colorless, clear | Colorless, clear | Colorless, clear | Colorless, clear |
| D | Colorless, clear | Colorless, clear | Colorless, clear | Colorless, clear | Colorless, clear |
| E | Colorless, clear | Colorless, clear | Colorless, clear | Colorless, clear | Colorless, clear |

TABLE 3 pH changes of conventional infusions

| ID | Prior to adding | After adding (h) | | | |
|---|---|---|---|---|---|
| | | 0 | 2 | 4 | 8 |
| A | 4.05 | 4.06 | 4.05 | 4.02 | 4.08 |
| B | 5.60 | 5.62 | 5.58 | 5.46 | 5.58 |
| C | 4.02 | 4.04 | 4.03 | 4.00 | 4.04 |
| D | 5.64 | 5.62 | 5.60 | 5.59 | 5.59 |
| E | 7.99 | 7.94 | 7.90 | 8.04 | 8.00 |

TABLE 4

Changes of YC-6 concentration in conventional infusions

| ID | 0 h | 2 h | 8 h | 24 h |
|---|---|---|---|---|
| A | 375.4 | 364.7 | 367.7 | 363.4 |
| B | 379.2 | 373.5 | 380.4 | 386.1 |
| C | 385.6 | 387.6 | 383.4 | 384.5 |
| D | 382.0 | 383.7 | 387.2 | 380.8 |
| E | 386.7 | 375.1 | 381.3 | 376.5 |

Example 7

Preliminary Evaluation on the Safety of YC-6

Kunming mice were caged by weight and randomly divided into 5 groups. Each group had 10 mice, with half males and half females. The YC-6 injection prepared in Example 3 (20 mg/ml) was i.v. administrated via tail vein at different doses. All mice were sacrificed after one-week observation. The toxic reaction and number of death of the animals were recorded every day. $LD_{50}$ and 95% confidence were calculated. $LD_{50}$ of YC-6 was more than 400±121 mg/kg.

Blood cells were prepared from fresh blood obtained from New Zealand rabbits according to conventional methods. The blood cells were diluted with saline to a 2% suspension. The YC-6 injection prepared in Example 1 was then added to the 2% suspension and incubated at 37° C. for 3 hours. Hemolysis rate was determined by using colorimetric method. Hemolysis rate of YC-6 injection was less than 1%.

Albino guinea pigs were subjected to anaphylactic test according to conventional procedures. No anaphylactic reaction was observed after intravenous administration of the YC-6 injection prepared in Example 1.

New Zealand rabbits were used to perform vascular stimulation test of intravenous administration of the YC-6 injection prepared in Example 1. The results showed that tissue changes of ear edge vein were similar between treatment group and control group. Each rabbit had integral vascular wall of ear edge vein and normal vein structure. No pathological change such as endothelial cells damage or surrounding tissue edema was observed.

The invention claimed is:

1. A composition, in the form of a liquid having at least one solvent or in the form of a solid, comprising 5α-androstane-3β,5,6β-triol and at least one soluble excipient, wherein the at least one soluble excipient comprises hydroxypropyl-β-cyclodextrin.

2. The composition of claim 1, wherein the weight ratio of 5α-androstane-3β,5,6β-triol to hydroxypropyl-β-cyclodextrin is 1-20:40-500.

3. The composition of claim 1, wherein the at least one soluble excipient further comprises at least one isotonic adjusting agent and/or at least one freeze drying filler.

4. The composition of claim 3, wherein the at least one isotonic adjusting agent is selected from sodium chloride, glucose, mannitol, lactose, xylitol, sorbitol, maltitol, and combinations thereof.

5. The composition of claim 3, wherein the at least one freeze-drying filler is selected from sodium chloride, glucose, mannitol, lactose, xylitol, sorbitol, maltitol, and combinations thereof.

6. The composition of claim 1, wherein the at least one solvent of the liquid injection is selected from propanediol, ethanol, polyethylene glycol 400, polyethylene glycol 200, glycerol, and water.

7. The composition of claim 3, comprising (by weight): 1-20 parts of 5α-androstane-3β,5,6β-triol, 4-500 parts of hydroxypropyl-β-cyclodextrin, 1-100 parts of an isotonic adjusting agent, 0-200 parts of a freeze drying filler, and 0-2000 parts of a solvent.

* * * * *